US012673913B2

(12) United States Patent
Utamura et al.

(10) Patent No.: US 12,673,913 B2
(45) Date of Patent: Jul. 7, 2026

(54) ALDEHYDE COMPOSITION

(71) Applicant: MITSUBISHI GAS CHEMICAL COMPANY, INC., Chiyoda-ku (JP)

(72) Inventors: Tatsuya Utamura, Okayama (JP); Junya Nishiuchi, Okayama (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 614 days.

(21) Appl. No.: 18/250,238

(22) PCT Filed: Nov. 2, 2021

(86) PCT No.: PCT/JP2021/040326

§ 371 (c)(1),
(2) Date: Apr. 24, 2023

(87) PCT Pub. No.: WO2022/102465

PCT Pub. Date: May 19, 2022

(65) Prior Publication Data

US 2023/0399284 A1 Dec. 14, 2023

(30) Foreign Application Priority Data

Nov. 12, 2020 (JP) ................................ 2020-188740

(51) Int. Cl.
*C11B 9/00* (2006.01)
*A61K 8/33* (2006.01)
*C07C 47/228* (2006.01)

(52) U.S. Cl.
CPC .......... *C07C 47/228* (2013.01); *C11B 9/0061* (2013.01)

(58) Field of Classification Search
CPC ..... C07C 45/73; C07C 47/228; C11B 9/0061; C11B 9/0015; A61K 8/33; A61Q 13/00
USPC ............................................ 512/21, 20, 8, 1
See application file for complete search history.

(56) References Cited

U.S. PATENT DOCUMENTS

| | | | |
|---|---|---|---|
| 3,801,709 | A | 4/1974 | Augsburger et al. |
| 4,968,668 | A | 11/1990 | Hafner et al. |
| 5,552,379 | A | 9/1996 | Winter et al. |
| 2016/0075627 | A1 | 3/2016 | Goeke et al. |

FOREIGN PATENT DOCUMENTS

| | | | |
|---|---|---|---|
| CN | 102627538 A | 8/2012 |
| CN | 103073403 A | 5/2013 |
| JP | 1-503536 A | 11/1989 |
| JP | 7-330653 A | 12/1995 |
| JP | 2016-523828 A | 8/2016 |

OTHER PUBLICATIONS

International Search Report issued Jan. 25, 2022, in PCT/JP2021/040326 (with English Translation), 7 pages.

Motoichi Indo, "Zoho Kaitei ban, Gosei Koryo:Kagaku to Shohin Chishiki (Enlarged and Revised Edition, Synthetic Perfume: Chemistry and Product Knowledge)", The Chemical Daily Co. Ltd., 1996, p. 213 to 215, and 228.

Shaikh, A.A. et al., "Preparation of optically active unsymmetrical ketones from (+)-acid halide", Journal of the Indian Chemical Society, (1966), vol. 43, No. 5, pp. 340-342.

Gerasimovich, T. B. et al., Synthesis of some fathaomatic—aldehydes, Zhurnal Obshchei Khimii,(1966), vol. 2, No. 4, pp. 670-672 (with English Translation).

Kologrivova, N. E. et al., Isomeric composition of aliphatic-aromatic aldehydes obtained from unsaturated aldehydes and aromatic hydrocarbons, Tr. Vses. Nauch-Issled. Inst. Sin. Natur. Dushist. Veshchestv, (1971), No. 9, pp. 96-101, CAPLUS [online], [retrieved on Jan. 7, 2022], Retrieved from: STN.

Gerasimovich, T.B. et al., "Synthesis of Some Aliphatic-Aromatic Aldehydes", Journal of Organic Chemistry USSR, Translated from Zhurnal Organicheskoi Khimii, vol. 2, No. 4, Apr. 1966, pp. 671-673, XP001247806.

Söhner, T. et al. "Halogen-free water-stable aluminates as replacement for persistent fluorinated weakly-coordinating anions", Green Chemistry, vol. 16, No. 11, Jan. 1, 2014, pp. 4696-4707, XP093040683.

Mutsuo Tanaka et al., "Formulation of aromatic compounds with CO in $HSO_3F$—$SbF_5$ under atmospheric pressure", J.Org.Chem., 1992, V.57, p. 2677-2680, [found online], [found Mar. 5, 2025], found from the Internet: https://pubs.acs.org/doi/10.1021/jo00035a024 , table 2.

Gerasimovich, T.B. et al., "Synthesis of Some Aliphatic-Aromatic Aldehydes", Journal of Organic Chemistry USSR, Translated from Zhurnal Organicheskoi Khimii, vol. 2, No. 4, Apr. 1966, pp. 670-672, XP001247806.

Kologrivova, N. E. et al., "Isomeric composition of aliphatic-aromatic aldehydes obtained from unsaturated aldehydes and aromatic hydrocarbons", Tr. Vses. Nauch-Issled. Inst. Sin. Natur. Dushist. Veshchestv, vol. 9, 1971, pp. 96-101 (with unedited computer-generated English translation).

*Primary Examiner* — Jessica Whiteley
(74) *Attorney, Agent, or Firm* — Oblon, McClelland, Maier & Neustadt, L.L.P.

(57) ABSTRACT

An aldehyde composition containing an aldehyde represented by Formula (1) and an aldehyde represented by Formula (2) is provided. A mass ratio [(1)/(2)] of the aldehyde represented by Formula (1) to the aldehyde represented by Formula (2) is from 96/4 to 99.97/0.03.

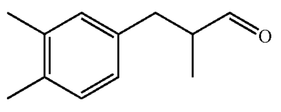

(1)

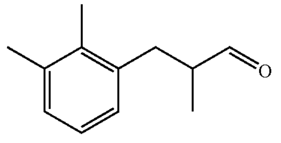

(2)

20 Claims, No Drawings

ALDEHYDE COMPOSITION

CROSS-REFERENCE TO RELATED APPLICATIONS

The present application is the national stage of international application PCT/JP2021/040326, filed on Nov. 2, 2021, and claims the benefit of the filing date of Japanese Appl. No. 2020-188740, filed on Nov. 12, 2020, the content of each of which is incorporated by reference.

TECHNICAL FIELD

The present invention relates to an aldehyde composition, a method for producing the same, and a perfume composition containing the aldehyde composition.

BACKGROUND ART

Some 3-(alkylphenyl)-2-alkylpropanols are known to be useful as compounded perfume raw materials.

For example, Non-Patent Literature 1 discloses that 3-(p-tert-butylphenyl)-2-methylpropanal (p-tert-butyl-α-methylhydrocinnamic aldehyde, Lilial) having a muguet-like (lilγ-of-the-valleγ-like) fragrance, 3-(p-isopropylphenyl)-2-methylpropanal (cyclamen aldehyde) having a cyclamen- and muguet-like (lilγ-of-the-valleγ-like) fragrance with a melon- and cucumber-like feeling, 3-(3,4-methylenedioxyphenyl)-2-methylpropanal (Helional) having a sweet heliotrope- and anise-like floral scent, and the like are useful as compounded perfume raw materials.

In addition, Patent Document 1 discloses a novel aromatic compound, such as 3-(5-tert-butyl-2-methyl-1-phenyl)propanal, as a compound having advantageous scent characteristics from the viewpoints of stability against oxidation and fragrance tenacity.

CITATION LIST

Non-Patent Literature

Non-Patent Literature 1: Motoichi Indo, "Zoho Kaitei ban, Gosei Koryo: Kagaku to Shohin Chishiki (Enlarged and Revised Edition, Synthetic Perfume: Chemistry and Product Knowledge)", The Chemical Daily Co. Ltd., 1996, p. 213 to 215, and 228

Patent Document

Patent Document 1: JP 07-330653 A

SUMMARY OF INVENTION

Technical Problem

In particular, floral perfumes and compounded perfumes are used in various fields, such as fragrance products, cosmetics, detergents, hygiene products, miscellaneous goods, pharmaceuticals, and food products. To increase the value of these products, new scents are being developed, and perfumes having a novel scent are in demand.

Thus, an object of the present invention is to provide an aldehyde composition having a floral and green-like scent with a fresh marine feeling, useful as a perfume, and useful also as a compounded perfume raw material.

Solution to Problem

The present inventors have synthesized and/or blended various aldehydes and compositions containing a plurality of those aldehydes and evaluated their fragrances, and found that specific aldehydes and compositions containing those aldehydes have an excellent scent and are excellent as raw materials for compounded perfumes, and completed the present invention.

That is, the present invention includes as follows.

[1] An aldehyde composition containing an aldehyde represented by Formula (1) below and an aldehyde represented by Formula (2) below, wherein a mass ratio [(1)/(2)] of the aldehyde represented by Formula (1) to the aldehyde represented by Formula (2) is from 96/4 to 99.97/0.03.

(1)

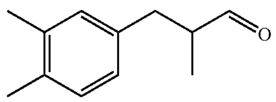

(2)

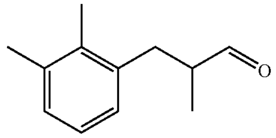

[2] A perfume composition containing the aldehyde composition described in [1].

[3] An aldehyde represented by Formula (1) below.

(1)

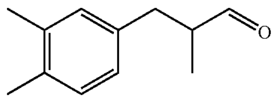

[4] A perfume composition containing the aldehyde described in [3].

[5] A method for producing an aldehyde, the method including, in this order, an aldol condensation step of subjecting a dimethylbenzaldehyde represented by General Formula (3) below and propionaldehyde to aldol condensation, and a hydrogenation step, the method producing an aldehyde represented by General Formula (4) below.

(3)

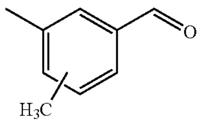

(4)

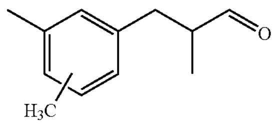

Advantageous Effects of Invention

According to the present invention, there can be provided the aldehyde composition having a floral and green-like scent with a fresh marine feeling, useful as a perfume, and useful also as a compounded perfume raw material.

DESCRIPTION OF EMBODIMENTS

Hereinafter, in the present specification, the expression "from XX to YY" means "XX or more and YY or less", "XX or higher and YY or lower", or "XX or greater and YY or less".

Aldehyde Composition

An aldehyde composition according to the present invention contains an aldehyde represented by Formula (1) below and an aldehyde represented by Formula (2) below, in which a mass ratio [(1)/(2)] of the aldehyde represented by Formula (1) to the aldehyde represented by Formula (2) is from 96/4 to 99.97/0.03.

(1)

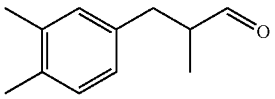

(2)

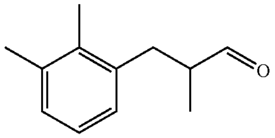

Aldehyde Represented by Formula (1)

The aldehyde represented by Formula (1) contained in the aldehyde composition of the present invention is 3-(3,4-dimethylphenyl)-2-methylpropanal. The aldehyde represented by Formula (1) has a floral scent with a marine feeling. The aldehyde represented by Formula (1) is also useful as a perfume and is useful also as a compounded perfume raw material.

Aldehyde Represented by Formula (2)

The aldehyde represented by Formula (2) contained in the aldehyde composition of the present invention is 3-(2,3-dimethylphenyl)-2-methylpropanal. The aldehyde composition of the present invention contains the aldehyde represented by Formula (2) and thus significantly improves the fresh marine feeling.

Composition, Etc. Of Aldehyde Composition

A total content of the aldehyde represented by Formula (1) and the aldehyde represented by Formula (2) in the aldehyde composition of the present invention is preferably 95 mass % or higher, more preferably 96 mass % or higher, and even more preferably 97 mass % or higher. The upper limit is not limited except that it is to be 100 mass % or lower.

A mass ratio [(1)/(2)] of the aldehyde represented by Formula (1) to the aldehyde represented by Formula (2) in the aldehyde composition of the present invention is from 96/4 to 99.97/0.03, preferably from 97/3 to 99.9/0.1, and more preferably from 98/2 to 99.5/0.5.

With the mass ratio of the aldehyde represented by Formula (1) to the aldehyde represented by Formula (2) in the above range, the aldehyde composition of the present invention has a floral and green-like scent with a particularly fresh marine feeling.

The content of the aldehyde represented by Formula (1) in the aldehyde composition of the present invention is preferably 96 mass % or higher, more preferably 97 mass % or higher, and even more preferably 98 mass % or higher, and preferably 99.97 mass % or lower, more preferably 99.9 mass % or lower, and even more preferably 99.5 mass % or lower.

The content of the aldehyde represented by Formula (2) in the aldehyde composition of the present invention is preferably 0.03 mass % or higher, more preferably 0.1 mass % or higher, and even more preferably 0.5 mass % or higher, and preferably 4 mass % or lower, more preferably 3 mass % or lower, and even more preferably 2 mass % or lower.

The aldehyde composition of the present invention may contain an unsaturated aldehyde represented by Formula (5) below, but the amount is preferably as small as possible, more preferably 2 mass % or lower, even more preferably 1 mass % or lower, still more preferably 0.5 mass % or lower, yet more preferably 0.1 mass % or lower, and still even more preferably the aldehyde composition does not contain the unsaturated aldehyde.

The unsaturated aldehyde represented by Formula (5) is 3-(3,4-dimethylphenyl)-2-methylpropenal.

The aldehyde composition of the present invention substantially does not contain the aldehyde represented by Formula (5) and thus has more freshness in the scent.

(5)

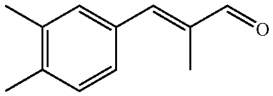

The aldehyde composition of the present invention may contain an alcohol represented by Formula (6) below.

The alcohol represented by Formula (6) is 3-(3,4-dimethylphenyl)-2-methylpropanol.

(6)

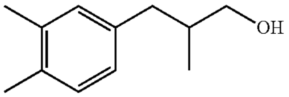

When the aldehyde composition of the present invention contains the alcohol represented by Formula (6) above, the content of the alcohol represented by Formula (6) above in the composition is preferably 0.03 mass % or higher and more preferably 0.05 mass % or higher, and preferably 3 mass % or lower and more preferably 1 mass % or lower.

The aldehyde composition of the present invention contains a small amount of the alcohol represented by Formula (6) and thus can further impart a marine feeling to the scent.

The aldehyde composition of the present invention having the composition described above has a floral and green-like scent with a fresh marine feeling and thus is useful as a perfume. In addition, the aldehyde composition of the present invention is useful also as a raw material for a compounded perfume (perfume composition) and can be used as a fragrance component of various products.

Perfume Composition

A perfume composition according to the present invention contains the aldehyde composition.

That is, the perfume composition of the present invention contains the aldehyde composition containing an aldehyde represented by Formula (1) below and an aldehyde represented by Formula (2) below, in which a mass ratio [(1)/(2)] of the aldehyde represented by Formula (1) to the aldehyde represented by Formula (2) is from 96/4 to 99.97/0.03.

Blending the aldehyde composition in a compounded perfume enhances a floral feeling and a heliotrope-like sweetness.

(1)

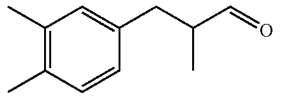

(2)

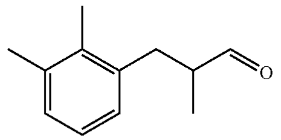

Furthermore, the perfume composition of the present invention may contain an alcohol represented by Formula (6) below.

(6)

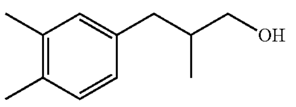

Furthermore, the aldehyde composition of the present invention preferably substantially does not contain an unsaturated aldehyde represented by Formula (5).

(5)

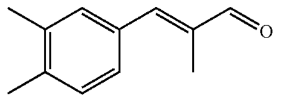

The content of the aldehyde composition in the perfume composition of the present invention is to be appropriately adjusted according to the type of perfume composition, the type of target fragrance, the intensity of the fragrance, and the like and is preferably from 0.01 to 90 mass % and more preferably from 0.1 to 50 mass %.

Examples of a perfume component that can be used in combination with the aldehyde composition in the perfume composition of the present invention include, but are not limited to, surfactants, such as polyoxyethylene lauryl sulfate ether; solvents, such as dipropylene glycol, diethyl phthalate, ethylene glycol, propylene glycol, methyl myristate, and triethyl citrate; and other perfume materials. Examples of the other perfume materials include hydrocarbons, such as limonene, α-pinene, β-pinene, terpinene, cedrene, longifolene, and valencene; alcohols, such as linalool, citronellol, geraniol, nerol, terpineol, dihydromyrcenol, ethyllinalool, farnesol, nerolidol, cis-3-hexenol, cedrol, menthol, borneol, β-phenylethyl alcohol, benzyl alcohol, phenyl hexanol, 2,2,6-trimethylcyclohexyl-3-hexanol, 1-(2-t-butylcyclohexyloxy)-2-butanol, 4-isopropylcyclohexane methanol, 4-methyl-2-(2-methylpropyl)tetrahydro-2H-pyran-4-ol, 2-methyl-4-(2,2,3-trimethyl-3-cyclopenten-1-yl)-2-butene-1-ol, 2-ethyl-4-(2,2,3-trimethyl-3-cyclopenten-1-yl)-2-buten-1-ol, isocamphylcyclohexanol, and 3,7-dimethyl-7-methoxyoctane-2-ol; phenols, such as eugenol, thymol, and vanillin; esters, such as linalyl formate, citronellyl formate, geranyl formate, n-hexyl acetate, cis-3-hexenyl acetate, linalyl acetate, citronellyl acetate, geranyl acetate, neryl acetate, terpinyl acetate, nopyl acetate, bornyl acetate, isobronyl acetate, o-t-butylcyclohexyl acetate, p-t-butylcyclohexyl acetate, tricyclodecenyl acetate, benzyl acetate, styralyl acetate, cinnamyl acetate, dimethylbenzylcarbinyl acetate, 3-pentyltetrahydropyran-4-yl acetate, citronellyl propionate, tricyclodecenyl propionate, allylcyclohexyl propionate, ethyl-2-cyclohexyl propionate, benzyl propionate, citronellyl butyrate, dimethylbenzylcarbinyl n-butyrate, tricyclodecenyl isobutyrate, methyl-2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyldihydro jasmonate, methyl-2,4-dihydroxγ-3,6-dimethyl benzoate, ethylmethylphenyl glycidate, methyl anthranilate, and frutate; aldehydes, such as n-octanal, n-decanal, n-dodecanal, 2-methylundecanal, 10-undecenal, citronellal, citral, hydroxycitronellal, dimethyl tetrahydrobenzaldehyde, 4(3)-(4-hydroxγ-4-methylpentyl)-3-cyclohexene-1-carboaldehyde, 2-cyclohexyl propanal, p-t-butyl-α-methylhydrocinnamic aldehyde, p-isopropyl-α-methylhydrocinnamic aldehyde, p-ethyl-α,α-dimethylhydrocinnamic aldehyde, α-amylcinnamic aldehyde, α-hexylcinnamic aldehyde, piperonal, and α-methyl-3,4-methylenedioxyhydrocinnamic aldehyde; ketones, such as methylheptenone, 4-methylene-3,5,6,6-tetramethyl-2-heptanone, amylcyclopentanone, 3-methyl-2-(cis-2-pentene-1-yl)-2-cyclopentene-1-on, methylcyclopentenolone, rose ketones, γ-methylionone, α-ionone, carbone, menthone, camphor, nootkatone, benzylacetone, anisylacetone, methyl-β-naphthylketone, 2,5-dimethyl-4-hydroxγ-3(2H)-furanone, maltol, 7-acetyl-1,2,3,4,5,6,7,8-octahydro-1,1,6,7-tetramethyl naphthalene, muscone, civetone, cyclopentadecanone, and cyclohexedecanone; acetals and ketals, such as acetoaldehyde ethylphenylpropyl acetal, citraldiethyl acetal, phenylacetoaldehyde glycerin acetal, and ethylacetoacetate ethyleneglycol ketals; ethers, such as anethole, β-naphthylmethyl ether, β-naphthylethyl ether, limonene oxide, rose oxide, 1,8-cineol, and racemic or photoactive dodecahydro-3a,6,6,9a-tetramethylnaphtho[2,1-b]furane; nitriles such as citronellyl nitrile; lactones, such as γ-nonalactone, γ-undecalactone, σ-decalactone, γ-jasmolactone, coumarin, cyclopentadecanolide, cyclohexadecanolide, ambrettolide, ethylene brassylate, and 11-oxahexadecanolide; and natural essential oils and natural extracts, such as orange, lemon, bergamot, mandarin, peppermint, spearmint, lavender, chamomile, rosemary, *eucalyptus*, sage, basil, rose, geranium, jasmine, ylang-ylang, anise, clove, ginger, nutmeg, cardamom, cedar, Japanese cypress, vetiver, patchouli, and labdanum. One of the other perfume materials may be individually blended, or two or more of them may be blended.

The perfume composition of the present invention can be used as a fragrance component in various products, such as perfumes and cosmetics, health and hygiene materials, miscellaneous goods, beverages, food products, quasi-drugs, and pharmaceuticals, to improve the fragrance of the product to which the perfume composition is blended.

The perfume composition of the present invention can be used as a fragrance component, for example, in fragrance products, such as perfumes and colognes; cosmetics for hair, such as shampoos, conditioners, hair tonics, hair creams, mousses, gels, pomades, and sprays; cosmetics for skin, such as lotions, beauty essences, creams, emulsions, packs, foundations, face powders, lipsticks, and makeup cosmetics; products for hygiene, such as dish washing detergents, laundry washing detergents, house detergents, glass cleaners, softeners, bleaching agents, indoor fragrances, and insecticides; quasi-drugs, such as toothpastes, mouthwashes, bath additives, antiperspirants, and permanent wave agents; miscellaneous goods, such as paper products; pharmaceuticals; and food products.

The content of the perfume composition of the present invention in the above products is to be appropriately adjusted according to the intensity of the fragrance required for each product and the like and is preferably from 0.001 to 50 mass % and more preferably from 0.01 to 20 mass %.

In addition, a perfume composition of another embodiment of the present invention contains the aldehyde represented by Formula (1). The aldehyde represented by Formula (1) is also useful as a perfume, and the content of the aldehyde represented by Formula (1) in the perfume composition is preferably from 0.01 to 90 mass % and more preferably from 0.1 to 50 mass %. Examples of the perfume component that can be used in combination with the aldehyde represented by Formula (1) include those described above.

Furthermore, the content of the perfume composition in each of these products is preferably from 0.001 to 50 mass % and more preferably from 0.01 to 20 mass %.

Method for Producing Aldehyde and Method for Producing Aldehyde Composition

The aldehyde constituting the aldehyde composition of the present invention may be obtained by any production method but is preferably obtained by a production method including, in this order, an aldol condensation step of subjecting a dimethylbenzaldehyde represented by General Formula (3) below and propionaldehyde to aldol condensation, and a hydrogenation step, the method producing an aldehyde represented by General Formula (4) below.

(3)

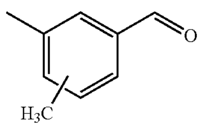

(4)

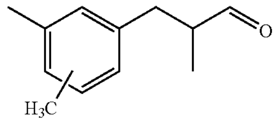

The aldehydes constituting the aldehyde composition of the present invention are at least the aldehyde represented by Formula (1) and the aldehyde represented by Formula (2), and reactions for producing these by the production method described above are represented by formulas below. The present production method will be described below.

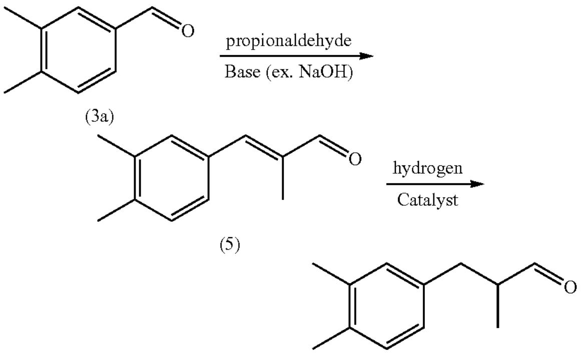

(3a) (5) (1)

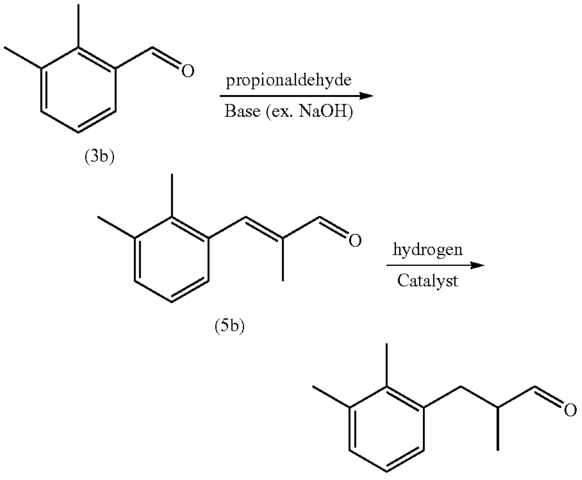

(3b) (5b) (2)

The aldehyde composition of the present invention contains the aldehyde represented by Formula (1) and the aldehyde represented by Formula (2) in a mass ratio [(1)/(2)] of the aldehyde represented by Formula (1) to the aldehyde represented by Formula (2) of 96/4 to 99.97/0.03. The aldehyde represented by Formula (1) and the aldehyde represented by Formula (2) may be respectively obtained by the method of the above formulas, and then these may be mixed and adjusted to give the above mass ratio; or the above raw materials or intermediates may be mixed and adjusted to give the above mass ratio.

In particular, in a case where 2,3-dimethylbenzaldehyde represented by Formula (3b) above is contained in a commercially available product of 3,4-dimethylbenzaldehyde represented by Formula (3a) above, which is a raw material, and the mass ratio [(1)/(2)] of the final product to be obtained falls within the above range when these raw materials are used, using the commercially available product of 3,4-dimethylbenzaldehyde as it is is simple and preferred.

Aldol Condensation Step

The method for producing the aldehyde of the present invention includes an aldol condensation step as a first step in which the aldehyde represented by Formula (3) and propionaldehyde are subjected to aldol condensation.

In the aldol condensation reaction in this step, a basic compound is preferably used as a catalyst.

The basic compound used as a catalyst is exemplified by sodium hydroxide, potassium hydroxide, sodium bicarbonate, or mixtures of these. The amount of the basic compound is preferably 0.05 equivalents or more, more preferably 0.1 equivalents or more, and even more preferably 0.2 equivalents or more, and preferably 3 equivalents or less, more preferably 1 equivalent or less, and even more preferably 0.5 equivalents or less per equivalent of the raw material dimethylbenzaldehyde.

The amount of propionaldehyde to be added is preferably 0.5 equivalents or more and more preferably 0.8 equivalents or more, and preferably 1.5 equivalents or less and more preferably 1.1 equivalents or less per equivalent of the raw material dimethylbenzaldehyde. Propionaldehyde is preferably added sequentially or continuously over time, and for example, is preferably added dropwise.

The aldol condensation reaction in this step is preferably carried out in a solvent.

The solvent is exemplified by various water-miscible organic solvents, specifically exemplified preferably by alcohols, such as methanol, ethanol, 1-propanol, 2-propanol, tert-butanol, allyl alcohol, ethylene glycol, propylene glycol, and diethylene glycol, and is more preferably methanol, ethanol, 1-propanol, 2-propanol, tert-butanol, ethylene glycol, propylene glycol, and diethylene glycol.

The reaction temperature in the aldol condensation reaction in this step is not particularly limited but is preferably 0° C. or higher and more preferably 10° C. or higher from the viewpoint of the reaction rate, and preferably 50° C. or lower, more preferably 40° C. or lower, and even more preferably 30° C. or lower from the viewpoint of preventing a side reaction.

The reaction time is not particularly limited and is to be a time in which the condensation sufficiently takes place but is preferably 10 minutes or more, more preferably 30 minutes or more, and even more preferably 1 hour or more, and preferably 24 hours or less, more preferably 12 hours or less, even more preferably 6 hours or less, and still more preferably 3 hours or less.

The reaction is to be stopped by neutralization; for example, the reaction can be stopped by adding an acid, such as acetic acid.

In addition, the method for isolating the intermediate represented by Formula (5) above and an intermediate represented by Formula (5b) above (3-(dimethylphenyl)-2-methylpropenal) from the solution after completion of the reaction is not particularly limited and to be carried out by appropriately combining liquid separation and extraction operations and purification by distillation.

For example, a low-polar or non-polar organic solvent is added to the solution after completion of the reaction to transfer the intermediate to the oil phase, and the resulting oil phase is dried, for example, with magnesium sulfate. The filtrate obtained by filtration is then concentrated, and further, the concentrate is purified by distillation, and the intermediate can be isolated accordingly.

<Hydrogenation Step>

The method for producing the aldehyde of the present invention includes a hydrogenation step after the aldol condensation step and produces the aldehyde represented by Formula (4) above.

This is a step in which the intermediate represented by Formula (5) above and the intermediate represented by Formula (5b) above obtained by the aldol condensation reaction are hydrogenated to obtain the target products, the aldehyde represented by Formula (1) and the aldehyde represented by Formula (2). The hydrogenation method is not particularly limited but can be carried out by a known method using a hydrogenation catalyst.

The hydrogenation catalyst is not particularly limited, and a known catalyst can be used. The hydrogenation catalyst is not particularly limited, and a known catalyst can be used, including, for example, a supported heterogeneous hydrogenation catalyst in which a metal, such as Ni, Pt, Pd, or Ru, is supported on carbon, silica, alumina, diatomaceous earth, or the like; a Ziegler-type hydrogenation catalyst prepared using a transition metal salt of Ni, Co, Fe, Cr, or the like, such as an organic acid salt and an acetylacetone salt, and a reducing agent, such as organoaluminum; and a homogeneous hydrogenation catalyst of what is called an organometallic complex or the like, such as an organometallic compound of Ti, Ru, Rh, Zr, or the like.

The temperature of the hydrogenation reaction in this step is preferably 0° C. or higher, more preferably 10° C. or higher, and even more preferably 20° C. or higher, and preferably 150° C. or lower and more preferably 100° C. or lower from the viewpoints of the reactivity and preventing a side reaction.

The pressure of hydrogen used in the hydrogenation reaction is preferably 0.01 MPaG or higher, more preferably 0.03 MPaG or higher, and even more preferably 0.05 MPaG or higher, and preferably 10 MPaG or lower, more preferably 3 MPaG or lower, even more preferably 1 MPaG or lower, and still more preferably 0.5 MPaG or lower.

The reaction time is not particularly limited but is preferably 3 minutes or more, more preferably 10 minutes or more, and even more preferably 30 minutes or more, and preferably 24 hours or less, more preferably 12 hours or less, and even more preferably 8 hours or less.

The hydrogenation reaction may be performed in the presence of a solvent. The solvent to be used is not particularly limited as long as the hydrogenation reaction is not inhibited but is exemplified by hydrocarbon solvents including: aliphatic hydrocarbons, such as pentane, hexane, isopentane, heptane, octane, and isooctane; aliphatic hydrocarbons, such as cyclopentane, methylcyclopentane, cyclohexane, methylcyclohexane, and ethylcyclohexane; and aromatic hydrocarbons, such as benzene, toluene, ethylbenzene, and xylene. One of these may be used individually, or two or more of these may be used in combination.

The method for isolating and purifying the target products, the aldehyde represented by Formula (1) and the aldehyde represented by Formula (2), from the solution after completion of the reaction is not particularly limited, and a known method is to be appropriately selected and carried out. Specifically, the method is exemplified by filtration, chromatography, and purification by distillation, and isolation by appropriately combining these can provide a high-purity target product, the aldehydes or aldehyde composition.

The aldehyde composition containing both the aldehyde represented by Formula (1) and the aldehyde represented by Formula (2) thus obtained has a floral and green-like scent with a fresh marine feeling and is useful as a perfume and useful also as a raw material for a compounded perfume (perfume composition). In addition, the aldehyde represented by Formula (1) is also useful as a perfume and useful also as a compounded perfume raw material.

The hydrogenation reaction in this step is further carried out, and as shown in the following reaction formula, an alcohol represented by Formula (6) below can also be obtained accordingly. The resulting aldehyde or composition contains a small amount of the alcohol represented by Formula (6) and thus can further impart a marine feeling to the scent.

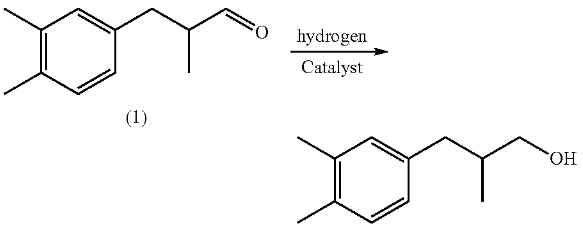

(1)

(6)

Another Production Method

The aldehyde represented by Formula (1) below and the aldehyde composition containing the aldehyde represented by Formula (1) below and the aldehyde represented by Formula (2) below may be obtained by a method other than the production method described above. For example, the aldehyde may be synthesized using a method in which an acetoxyenol intermediate is synthesized by a reaction between ortho-xylene and 2-methyl-3,3-diacetoxypropene and then hydrolyzed as shown in the following reaction formula.

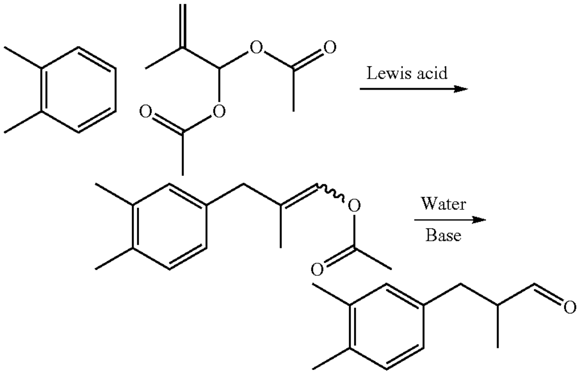

(1)

According to this method, the aldehyde represented by Formula (2) below is also produced as a by-product resulting from the production of an isomer of an enol intermediate in the reaction between ortho-xylene and 2-methyl-3,3-diacetoxypropene as shown in the following reaction formula, and thus the aldehyde composition containing the aldehyde represented by Formula (1) and the aldehyde represented by Formula (2) can also be obtained by one reaction.

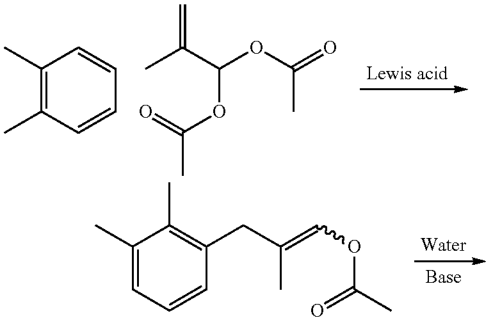

-continued

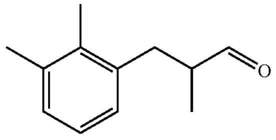

(2)

EXAMPLES

The present invention will be described specifically based on Examples described below, but the present invention is not limited to these Examples.

Analysis of Composition

The composition in each step described later, the composition of the product, and the composition of the composition were determined using gas chromatography (GC-2010 Plus, available from Shimadzu Corporation) by preparing a calibration curve using n-decane (reagent grade, available from FUJIFILM Wako Pure Chemical Corporation) as an internal standard material.

A capillary column HR-1701 (0.32 mm cp in inner diameter and 30 m in length) available from Agilent Technologies Japan, Ltd. was used. The heating program increased the temperature from 100° C. to 280° C. at a rate of 5° C./min and maintained for 30 minutes.

NMR Spectral Analysis

Instrument: Varian NMR System PS600 600 MHz
Solvent: deuterated chloroform ($CDCl_3$)
Measurement mode: $^1H$, $^{13}C$
Internal standard substance: tetramethylsilane (TMS)

Evaluation of Scent/Fragrance Note

The scent and fragrance note of aldehyde compositions and perfume compositions obtained in examples and comparative examples were evaluated by a method in which filter paper 8 mm in width and 15 cm in length was impregnated with the composition, and an expert panelist smelled the filter paper.

Raw Materials

The following raw materials were used in examples and comparative examples.

3,4-Dimethylbenzaldehyde: available from Mitsubishi Gas Chemical Company, Inc.

2,3-Dimethylbenzaldehyde: available from Tokyo Chemical Industry Co., Ltd.

Propionaldehyde: available from FUJIFILM Wako Pure Chemical Corporation

Methanol: guaranteed reagent available from FUJIFILM Wako Pure Chemical Industries, Ltd.

Heptane: guaranteed reagent available from FUJIFILM Wako Pure Chemical Corporation 50% Sodium hydroxide: available from FUJIFILM Wako Pure Chemical Corporation Acetic acid: available from FUJIFILM Wako Pure Chemical Corporation Sodium carbonate: available from FUJIFILM Wako Pure Chemical Corporation 10% Palladium-carbon catalyst: water-containing product, PE type, available from N.E. Chemcat Corporation n-Decane: available from FUJIFILM Wako Pure Chemical Corporation

Production of Aldehyde

Example 1: 3-(3,4-Dimethylphenyl)-2-Methylpropanal (Formula (1))

Aldol Condensation Step

In a 500-mL round-bottom flask equipped with a stirrer, a thermometer, and a dropping funnel were placed methanol (100.0 g), a 50% sodium hydroxide aqueous solution (14.3 g), and 3,4-dimethylbenzaldehyde (purity of 99.95 mass %, 2,3-dimethylbenzaldehyde content of 0.01 mass %, 100.0 g) and cooled to 15° C. with stirring, and then propionaldehyde (43.6 g) was added dropwise over 1 hour. After completion of the dropwise addition, the mixture was maintained at for 1 hour, and the reaction was completed. Acetic acid (10.8 g) was added to the mixture to neutralize, then water and heptane were added, and the aqueous phase was separated by liquid separation. Heptane was then distilled off, and a crude intermediate solution was obtained. This crude intermediate solution was subjected to simple distillation (from 116 to 120° C./2 torr), and an intermediate solution containing 3-(3,4-dimethylphenyl)-2-methylpropenal (Formula (5)) was obtained as an intermediate.

Hydrogenation Step

In a 200-mL stainless steel autoclave equipped with a magnetic induction stirrer and capable of controlling the internal temperature with a jacket were placed the intermediate solution (64.0 g) obtained in the aldol condensation step, a 5% sodium carbonate aqueous solution (30.0 g), and a 10% palladium-carbon catalyst (water-containing product, PE type, available from N.E. Chemcat Corporation, 1.0 g) and stirred at 75° C. under a hydrogen pressure of 0.4 MPa for 6 hours to carry out hydrogenation reaction. The reaction solution was filtered to remove the catalyst, heptane was added, and the aqueous phase was separated by liquid separation. Heptane was then distilled off, and a crude composition was obtained. The crude composition was rectified at 10 torr using a rectifying column with a theoretical plate number of 20, and 3-(3,4-dimethylphenyl)-2-methylpropanal (Formula (1)) (21.0 g, containing 0.01 mass % of 3-(2,3-dimethylphenyl)-2-methylpropanal (Formula (2)) was obtained as a fraction at 125 to 126° C. The results of the NMR spectral measurement are indicated below. The evaluation results of the scent/fragrance note of the resulting aldehyde are shown in Table 1.

Results of NMR Spectral Measurements of 3-(3,4-Dimethylphenyl)-2-Methylpropanal (Formula (1))

$^{1}$H NMR (600 MHz, $CDCl_3$) δ 1.08 (3H, d, J=7.2 Hz), 2.23 (3H, s), 2.24 (3H, s), 2.54 (1H, dd, J=13.8 Hz, 8.4 Hz), 2.63-2.67 (1H, m), 3.01 (1H, dd, J=13.8 Hz, 6.0 Hz), 6.90 (1H, dd, J=7.5 Hz, 1.5 Hz), 6.94 (1H, s), 7.05 (1H, d, J=7.8), 9.71 (1H, s)

$^{13}$C NMR (150 MHz, $CDCl_3$) δ 13.3, 19.3, 19.8, 36.3, 48.1, 126.3, 129.7, 130.3, 134.6, 136.1, 136.7, 204.7

Production Example 1: 3-(2,3-Dimethylphenyl)-2-Methylpropanal (Formula (2))

3-(2,3-Dimethylphenyl)-2-methylpropanal (Formula (2)) (9.0 g, containing 0.08 mass % of 3-(3,4-dimethylphenyl)-2-methylpropanal (Formula (1))) was obtained in the same manner as in Example 1 except that 2,3-dimethylbenzaldehyde (purity of 99.0%, 25.0 g) was used in place of 3,4-dimethylbenzaldehyde. The results of the NMR spectral measurement are shown below. The evaluation results of the scent/fragrance note of the resulting aldehyde are shown in Table 1.

Results of NMR Spectral Measurement of 3-(2,3-Dimethylphenyl)-2-Methylpropanal (Formula (2))

$^{1}$H NMR (600 MHz, $CDCl_3$) δ 1.10 (3H, d, J=7.2 Hz), 2.21 (3H, s), 2.28 (3H, s), 2.56-2.65 (2H, m), 3.14 (1H, dd, J=13.8 Hz, 6.0 Hz), 6.97 (1H, dd, J=6.3 Hz, 2.1 Hz), 7.02-7.05 (2H, m), 9.72 (1H, s)

$^{13}$C NMR (150 MHz, $CDCl_3$) δ 13.5, 15.3, 20.8, 34.6, 47.1, 125.4, 127.9, 128.3, 134.6, 136.9, 137.2, 204.6

Production Example 2: 3-(3,4-Dimethylphenyl)-2-Methylpropenal (Formula (5))

Aldol Condensation Step

In a 500-mL round-bottom flask equipped with a stirrer, a thermometer, and a dropping funnel were placed methanol (100.0 g), a 50% sodium hydroxide aqueous solution (14.3 g), and 3,4-dimethylbenzaldehyde (purity of 99.2 mass %, 2,3-dimethylbenzaldehyde content of 0.69 mass %, 100.0 g) and cooled to 15° C. with stirring, and then propionaldehyde (43.6 g) was added dropwise over 1 hour. After completion of the dropwise addition, the mixture was maintained at for 1 hour, and the reaction was completed. Acetic acid (10.8 g) was added to the mixture to neutralize, then water and heptane were added, and the aqueous phase was separated by liquid separation. Heptane was then distilled off, and a crude intermediate solution was obtained. This crude intermediate solution was subjected to simple distillation (from 116 to 120° C./2 torr) and further rectified using a rectifying column with a theoretical plate number of 20, and 3-(3,4-dimethylphenyl)-2-methylpropenal (Formula (5)) (10.0 g, purity of 98.08 mass %) was obtained.

Production of Aldehyde Composition

Example 2

Aldol Condensation Step

In a 500-mL round-bottom flask equipped with a stirrer, a thermometer, and a dropping funnel were placed methanol (100.0 g), a 50% sodium hydroxide aqueous solution (14.3 g), and 3,4-dimethylbenzaldehyde (purity of 99.2 mass %, 2,3-dimethylbenzaldehyde content of 0.69 mass %, 100.0 g) and cooled to 15° C. with stirring, and then propionaldehyde (43.6 g) was added dropwise over 1 hour. After completion of the dropwise addition, the mixture was maintained at for 1 hour, and the reaction was completed. Acetic acid (10.8 g) was added to the mixture to neutralize, then water and heptane were added, and the aqueous phase was separated by liquid separation. Heptane was then distilled off, and a crude intermediate solution was obtained. This crude intermediate solution was subjected to simple distillation (from 116 to 120° C./2 torr), and an intermediate solution containing 92.2% of 3-(3,4-dimethylphenyl)-2-methylpropenal (Formula (5)) and 0.7% of 3-(2,3-dimethylphenyl)-2-methylpropenal (Formula (5b)) was obtained as an intermediate.

Hydrogenation Step

In a 200-mL stainless steel autoclave equipped with a magnetic induction stirrer and capable of controlling the internal temperature with a jacket were placed the intermediate solution (64.0 g) obtained in the aldol condensation step, a 5% sodium carbonate aqueous solution (30.0 g), and a 10% palladium-carbon catalyst (water-containing product, PE type, available from N.E. Chemcat Corporation, 1.0 g) and stirred at 75° C. under a hydrogen pressure of 0.4 MPa for 6 hours to carry out hydrogenation reaction. The reaction solution was filtered to remove the catalyst, heptane was added, and the aqueous phase was separated by liquid separation. Heptane was then distilled off, and a crude composition (3-(3,4-dimethylphenyl)-2-methylpropanal purity of 91.0%) was obtained. The crude composition was rectified at 10 torr using a rectifying column with a theoretical plate number of 20, and an aldehyde composition (20.0 g) containing 3-(3,4-dimethylphenyl)-2-methylpropanal (Formula (1)) and 3-(2,3-dimethylphenyl)-2-methylpropanal (Formula (2)) was obtained as a fraction at 125 to 126° C. The composition and evaluation results of the scent/fragrance note of the resulting aldehyde composition are shown in Table 1.

Examples 3 and 4 and Comparative Example 1

The aldehyde obtained in Production Example 1 and the aldehyde obtained in Production Example 2 were added to the aldehyde composition obtained in Example 2, a ratio of each component was adjusted to the ratio shown in Table 1, and each aldehyde composition was obtained. The composition and evaluation results of the scent/fragrance note of the resulting aldehyde are indicated in Table 1.

TABLE 1

| | | Example 1 | Example 2 | Example 3 | Comparative Example 1 | Example 4 | Production Example 1 | Production Example 2 |
|---|---|---|---|---|---|---|---|---|
| 3-(3,4-Dimethylphenyl)-2-methylpropanal (Formula (1)) | mass % | 99.45 | 98.70 | 96.39 | 94.75 | 97.88 | 0.08 | 0.00 |
| 3-(2,3-Dimethylphenyl)-2-methylpropanal (Formula (2)) | mass % | 0.01 | 0.97 | 3.24 | 4.84 | 0.92 | 99.12 | 0.00 |
| (1)/(2) | Mass ratio | 99.99/0.01 | 99.03/0.97 | 96.75/3.25 | 95.14/4.86 | 99.07/0.93 | 0.08/99.92 | — |
| 3-(3,4-Dimethylphenyl)-2-methylpropanol (Formula (6)) | mass % | 0.04 | 0.11 | 0.10 | 0.10 | 0.09 | 0.00 | 0.00 |
| 3-(3,4-Dimethylphenyl)-2-methylpropenal (Formula (5)) | mass % | 0.01 | 0.00 | 0.00 | 0.00 | 0.82 | 0.00 | 98.08 |
| Other | mass % | 0.49 | 0.22 | 0.27 | 0.31 | 0.30 | 0.80 | 1.92 |
| Scent/fragrance note | | Floral, Green, Marine, Muguet, Heliotrope | Floral, Green, Marine, Muguet, Heliotrope | Floral, Green, Marine, Muguet, Heliotrope | Floral, Green, Marine, Muguet, Heliotrope | Floral, Green, Marine, Muguet, Heliotrope | Woody, Green, Floral, Powdery, Spicy | — |
| Scent characteristics | | Heliotrope-like floral scent with a marine feeling. | Helional-like fresh marine feeling. | Helional-like fresh marine feeling. | Helional-like scent but with weak aldehyde feeling and marine feeling. | Helional-like fresh marine feeling. | α-Pinene-like fresh feeling. | — |
| Comparison with Example 2 | | Floral feeling increased. Weak freshness. | — | Almost no difference from Example 2 and having very slightly weaker floral feeling. | Entirely flat and metallic. | Slightly dry lingering scent after 24 hours. | — | — |

Example 5 and Comparative Example 2: Floral-Fruity-Like Perfume Composition (for Detergents)

The aldehyde composition obtained in Example 2 or Lilial (3-(p-tert-butylphenyl)-2-methylpropanal) was each added in an amount of 3.5 mass % to a compounded perfume base shown in Table 2, and the scent/fragrance note was evaluated.

TABLE 2

(mass %)

| | Example 5 | Comparative Example 2 |
|---|---|---|
| LILIAL (3-(p-tert-butylphenyl)-2-methylpropanal) | — | 3.5 |
| Aldehyde composition of Example 2 ((1)/(2) = 99.03/0.97) | 3.5 | — |
| ALDEHYDE C-14 | 2 | 2 |

TABLE 2-continued

| | Example 5 | (mass %) Comparative Example 2 |
|---|---|---|
| ALLYL OENANTHATE | 1.6 | 1.6 |
| ISO E SUPER | 2.5 | 2.5 |
| AMBROXAN | 0.1 | 0.1 |
| CITRONELLOL | 2.5 | 2.5 |
| CYCLAPROP | 8.5 | 8.5 |
| CYCLO HEXYL SALICYLATE | 1 | 1 |
| CYCLVERTAL = VERTOLIFF | 0.4 | 0.4 |
| DAMASCENONE | 0.3 | 0.3 |
| DIHYDRO MYRCENOL | 2 | 2 |
| DPG | 8.45 | 8.45 |
| DYNASCONE 10 DPG | 0.7 | 0.7 |
| ETHYL BENZOATE | 0.15 | 0.15 |
| ETHYL-2-METHYL BUTYRATE | 1 | 1 |
| EXALTOLIDE TOTAL | 2.5 | 2.5 |
| GERANYL ACETATE | 2 | 2 |
| HABANOLDE | 4 | 4 |
| HELIOTROPINE | 0.5 | 0.5 |
| HEXYL CINNAMIC ALDEHYDE | 1.2 | 1.2 |
| ISO AMYL BUTYRATE | 0.3 | 0.3 |
| LINALOOL | 8 | 8 |
| MELUSAT | 2.8 | 2.8 |
| METHYL IONONE GAMMA | 4 | 4 |
| MYRAC ALDEHYDE | 0.2 | 0.2 |
| ORANGE OIL VALENCIA 5-FOLD | 2 | 2 |
| PHENOSANOL | 2.5 | 2.5 |
| PHENYL ETHYL ALCOHOL | 3.5 | 3.5 |
| POIRENATE | 4.5 | 4.5 |
| PRENYL ACETATE | 0.6 | 0.6 |
| UNDECAVERTOL | 0.2 | 0.2 |
| VERDOX | 12 | 12 |
| VERTENEX | 9 | 9 |
| FRUITATE | 5.5 | 5.5 |
| Total | 100 | 100 |

The perfume composition of Example 5 had enhanced Heliotrope-like sweetness and floral feeling compared with the perfume composition of Comparative Example 2.

Example 6 and Comparative Example 3: Fruity/Floral-Like Perfume Composition (for Body Care)

The aldehyde composition obtained in Example 2 or Helional (3-(3,4-methylenedioxyphenyl)-2-methylpropanal) was each added in an amount of 2.5 mass % to a compounded perfume base shown in Table 3, and the scent/fragrance note was evaluated.

TABLE 3

| | Example 6 | (mass %) Comparative Example 3 |
|---|---|---|
| Helional (3-(3,4-methylenedioxyphenyl)-2-methylpropanal) | — | 2.5 |
| Aldehyde composition of Example 2 ((1)/(2) = 99.03/0.97) | 2.5 | — |
| ALDEHYDE C-14 | 0.3 | 0.3 |
| Allyl cyclohexyl propionate | 0.3 | 0.3 |
| Allyl oenanthate | 0.1 | 0.1 |
| Ambermax 10 tec | 0.7 | 0.7 |
| Amberose | 3 | 3 |
| Ambroxan | 0.1 | 0.1 |
| Benzyl acetate | 0.5 | 0.5 |
| Blueberry base | 0.2 | 0.2 |
| cis-jasmone | 0.1 | 0.1 |
| cis-3-hexenyl acetate | 0.1 | 0.1 |
| cis-3-hexenyl salicylate | 2.8 | 2.8 |
| Citronellol | 1.3 | 1.3 |

TABLE 3-continued

| | Example 6 | (mass %) Comparative Example 3 |
|---|---|---|
| Citronellyl acetate | 0.6 | 0.6 |
| Damascone alpha | 0.16 | 0.16 |
| Decalactone gamma | 0.3 | 0.3 |
| DPG | 17.4 | 17.4 |
| Ethyl acetoacetate | 0.2 | 0.2 |
| Ethyl butyrate | 0.04 | 0.04 |
| Ethyl linalool | 2.2 | 2.2 |
| Ethyl maltol | 0.14 | 0.14 |
| Ethylene brassylate | 12.5 | 12.5 |
| Florol | 8 | 8 |
| Habanolide | 7 | 7 |
| Hedione | 26 | 26 |
| Hexyl acetate | 0.5 | 0.5 |
| Ionone beta | 1 | 1 |
| Ligustral | 0.1 | 0.1 |
| Magnolan | 2 | 2 |
| Manzanate | 0.04 | 0.04 |
| Methyl ionone gamma | 2 | 2 |
| Nonalactone gamma | 0.1 | 0.1 |
| Orange oil florida | 2 | 2 |
| Phenyl acetaldehyde 50 PEA | 0.04 | 0.04 |
| Phenylethyl alcohol | 0.5 | 0.5 |
| Raspberry ketone | 0.2 | 0.2 |
| Rose oxide | 0.06 | 0.06 |
| Sandela | 0.7 | 0.7 |
| Styrallyl acetate | 0.3 | 0.3 |
| Undecavertol | 0.6 | 0.6 |
| Veloutone | 0.32 | 0.32 |
| Veerdox | 3 | 3 |
| Total | 100 | 100 |

The perfume composition of Example 6 had a stronger potency, an increased floral feeling, and more volume compared with the perfume composition of Comparative Example 3.

Example 7 and Comparative Example 4: Floral/Green-Like Perfume Composition (for Body Care)

The aldehyde composition obtained in Example 2 or Bourgeonal (3-(4-tert-butylphenyl)propanal) was each added in an amount of 3 mass % to a compounded perfume base shown in Table 4, and the scent/fragrance note was evaluated.

TABLE 4

| | Example 7 | (mass %) Comparative Example 4 |
|---|---|---|
| Bourgeonal (3-(4-tert-butylphenyl)propanal) | — | 3 |
| Aldehyde composition of Example 2 ((1)/(2) = 99.03/0.97) | 3 | — |
| ALDEHYDE C-14 | 0.5 | 0.5 |
| ALDEHYDE C-16 | 0.5 | 0.5 |
| Allyl cyclohexyl propionate | 1 | 1 |
| Amyl cinnamic aldehyde | 8 | 8 |
| Anisaldehyde | 0.5 | 0.5 |
| Benzyl acetate | 2.6 | 2.6 |
| cis-3-Hexenol | 0.6 | 0.6 |
| Citronellol | 2 | 2 |
| Citronellyl nitrile | 0.2 | 0.2 |
| Cyclamen aldehyde | 1.5 | 1.5 |
| Damascone delta | 0.1 | 0.1 |
| Decalactone gamma | 0.4 | 0.4 |
| DPG | 3.6 | 3.6 |
| Ethyl vanillin | 0.05 | 0.05 |
| Ethyl-2-methyl butyrate | 0.3 | 0.3 |

TABLE 4-continued

| | Example 7 | (mass %) Comparative Example 4 |
|---|---|---|
| Florol | 9 | 9 |
| Geranyl acetate | 0.3 | 0.3 |
| Hedione | 25 | 25 |
| Hexyl acetate | 0.6 | 0.6 |
| Hexyl salicylate | 5 | 5 |
| Ligustral | 0.2 | 0.2 |
| Linalool | 8 | 8 |
| Linalyl acetate | 3 | 3 |
| Melonal | 0.1 | 0.1 |
| Methyl anthranilate | 0.1 | 0.1 |
| Methyl ionone gamma | 5 | 5 |
| Methyl octyne carbonate | 0.15 | 0.15 |
| Musk 50 BB | 12 | 12 |
| Orange oil florida | 4 | 4 |
| Prenyl acetate | 0.2 | 0.2 |
| Raspberry ketone | 0.2 | 0.2 |
| Styrallyl acetate | 0.8 | 0.8 |
| Terpineol | 1.5 | 1.5 |
| Total | 100 | 100 |

The perfume composition of Example 7 had an increased white floral feeling with a clean feeling and a wider range of scents compared with the perfume composition of Comparative Example 4.

Example 8 and Comparative Example 5: Floral/Green-Like Perfume Composition (for Fabric Care)

The aldehyde composition obtained in Example 2 or Bourgeonal (3-(4-tert-butylphenyl)propanal) was each added in an amount of 12 mass % to a compounded perfume base shown in Table 5, and the scent/fragrance note was evaluated.

TABLE 5

| | Example 8 | (mass %) Comparative Example 5 |
|---|---|---|
| Bourgeonal (3-(4-tert-butylphenyl)propanal) | — | 12 |
| Aldehyde composition of Example 2 ((1)/(2) = 99.03/0.97) | 12 | — |
| Amberone | 20 | 20 |
| Amyl salicylate | 1.8 | 1.8 |
| Anisaldehyde | 1.8 | 1.8 |
| Benzaldehyde | 0.04 | 0.04 |
| Benzyl acetate | 2 | 2 |
| cis-3-Hexenyl acetate | 0.04 | 0.04 |
| Cyclamen aldehyde | 0.35 | 0.35 |
| Cyclaprop | 2.5 | 2.5 |
| Damascone delta | 0.13 | 0.13 |
| DPG | 6.51 | 6.51 |
| Floralozone | 0.1 | 0.1 |
| Florol | 8.5 | 8.5 |
| Hedione | 4.5 | 4.5 |
| Helional | 3.5 | 3.5 |
| Ionone alpha | 2.5 | 2.5 |
| Jasmacyclene | 8 | 8 |
| Koavone | 1.3 | 1.3 |
| Ligustral | 0.5 | 0.5 |
| Linalool | 2.5 | 2.5 |
| Methyl anthranilate | 0.27 | 0.27 |
| Methyl ionone gamma | 15 | 15 |
| Oranger crystals | 0.53 | 0.53 |
| Phenyl ethyl acetate | 2.5 | 2.5 |

TABLE 5-continued

| | Example 8 | (mass %) Comparative Example 5 |
|---|---|---|
| Phenyl ethyl alcohol | 2.5 | 2.5 |
| Prenyl acetate | 0.1 | 0.1 |
| Undecavertol | 0.17 | 0.17 |
| Violiff | 0.36 | 0.36 |
| Total | 100 | 100 |

While the perfume composition of Comparative Example 5 had a strong aldehyde feeling, the perfume composition of Example 8 had an increased white floral feeling and integrated and very sophisticated scents.

The results of Examples reveal that the aldehyde composition of the present invention has a floral and green-like scent with a fresh marine feeling and thus is useful as a perfume. Furthermore, the aldehyde composition when blended in a compounded perfume enhances a floral feeling and a heliotrope-like sweetness and is found to be useful also as a raw material for a compounded perfume.

In addition, the aldehyde represented by Formula (1) of the present invention also has a floral scent with a marine feeling and thus is found to be useful as a perfume.

The invention claimed is:

1. An aldehyde composition, comprising:

a first aldehyde of formula (1):

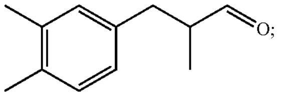

(1)

a second aldehyde of formula (2):

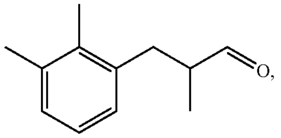

(2)

wherein a (1)/(2) mass ratio of the first aldehyde of formula (1) to the second aldehyde of formula (2) is in a range of from 96/4 to 99.97/0.03.

2. A perfume composition, comprising:

the aldehyde composition of claim 1.

3. A method for producing an aldehyde, the method comprising, in this order:

subjecting a dimethylbenzaldehyde of formula (3):

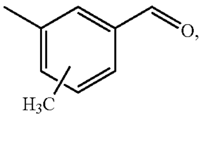

(3)

and propionaldehyde to aldol condensation, to obtain an intermediate; and hydrogenating the intermediate to obtain an aldehyde of formula (4):

(4)

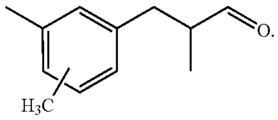

4. The method of claim 3, wherein the hydrogenating yields an aldehyde of formula (1):

(1)

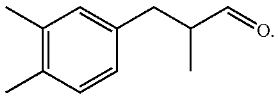

5. The method of claim 3, wherein the hydrogenating yields an aldehyde of formula (2):

(2)

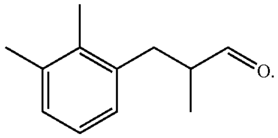

6. The aldehyde composition of claim 1, further comprising:

an alcohol of formula (6)

(6)

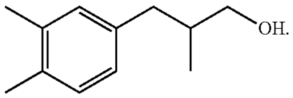

7. The aldehyde composition of claim 1, wherein the (1)/(2) mass ratio is in a range of from 96/4 to 99.07/0.93.

8. The aldehyde composition of claim 1, wherein the (1)/(2) mass ratio is in a range of from 96/4 to 99.03/0.97.

9. The aldehyde composition of claim 1, wherein the (1)/(2) mass ratio is in a range of from 96/4 to 96.75/3.25.

10. The aldehyde composition of claim 1, wherein the (1)/(2) mass ratio is in a range of from 96.75/3.25 to 99.97/0.03.

11. The aldehyde composition of claim 1, wherein the (1)/(2) mass ratio is in a range of from 99.03/0.97 to 99.97/0.03.

12. The aldehyde composition of claim 1, wherein the (1)/(2) mass ratio is in a range of from 99.07/0.93 to 99.97/0.03.

13. The aldehyde composition of claim 1, wherein the (1)/(2) mass ratio is in a range of from 97/3 to 99.9/0.1.

14. The aldehyde composition of claim 1, wherein the (1)/(2) mass ratio is in a range of from 98/2 to 99.5/0.5.

15. The aldehyde composition of claim 1, comprising the first aldehyde and the second aldehyde, in total, in at least 95 mass %.

16. The aldehyde composition of claim 1, comprising the first aldehyde and the second aldehyde, in total, in at least 96 mass %.

17. The aldehyde composition of claim 1, comprising the first aldehyde and the second aldehyde, in total, in at least 97 mass %.

18. The aldehyde composition of claim 1, comprising the first aldehyde in a range of from 96 to 99.97 mass %.

19. The aldehyde composition of claim 1, comprising the first aldehyde in a range of from 97 to 99.9 mass %.

20. The aldehyde composition of claim 1, comprising the first aldehyde in a range of from 98 to 99.5 mass %.

* * * * *